United States Patent [19]

Terrel et al.

[11] Patent Number: 5,365,793
[45] Date of Patent: Nov. 22, 1994

[54] EQUIPMENT AND METHOD FOR ENVIRONMENTAL TESTING OF BITUMINOUS SPECIMENS

[75] Inventors: Ronald L. Terrel, Edmonds, Wash.; Saleh Al-Swailmi, Riyadh, Saudi Arabia; Todd V. Scholz, Portland, Oreg.

[73] Assignee: State of Oregon Acting By and Through Oregon State University, Corvalis, Oreg.

[21] Appl. No.: 25,047

[22] Filed: Mar. 1, 1993

[51] Int. Cl.⁵ .................... G01N 3/32; G01N 3/18; G01N 15/08
[52] U.S. Cl. .................................. 73/813; 73/38
[58] Field of Search .............. 73/813, 794, 819, 153, 73/38

[56] References Cited

U.S. PATENT DOCUMENTS

| | | | |
|---|---|---|---|
| 3,854,328 | 12/1974 | Schmidt | 73/813 |
| 4,096,742 | 6/1978 | Musolf et al. | 73/813 |
| 4,753,107 | 6/1988 | Reed et al. | 73/38 |

*Primary Examiner*—Thomas P. Noland
*Attorney, Agent, or Firm*—Seed & Berry

[57] ABSTRACT

A testing system for determining the water sensitivity of a compacted asphalt concrete specimen under various conditions isolates the specimen on a test stand in an environmental cabinet by an impervious shroud and end platens connected to an external fluid circulating system. The specimen is loaded via a load cell by a pulsating actuator and a transducer on the specimen measures axial deformation. Data is transferred from the load cell and transducer to a micro-computer system for analysis.

15 Claims, 4 Drawing Sheets

EQUIPMENT AND METHOD FOR ENVIRONMENTAL TESTING OF BITUMINOUS SPECIMENS

This invention was made with government support under a grant from the Strategic Highway Research Program of the National Research Council. Contract #SHRP-87-A003A.

TECHNICAL FIELD

The present invention is directed to a testing system for determining the water sensitivity of compacted asphalt concrete mixtures under various temperature and load conditions to predetermine their suitability for use as a highway paving material. The information gathered by the testing system is useful to compare and select various asphalt binders, modifiers, additives, mixtures, and aggregates to maximize highway performance.

BACKGROUND OF THE INVENTION

Research indicates that permeability of asphalt concrete plays a significant role in performance, particularly in the presence of water. For example, if asphalt concrete is conditioned by water saturation followed by freezing and thawing the retained strength or modulus is typically somewhat lower than for the original dry mixture.

Most asphalt pavements in the United States have an average of about 5-10% air voids. Sufficient of these voids are connected to provide some permeability, but not sufficient permeability for free drainage. Hence, water is commonly trapped within the asphalt concrete and has a deleterious effect, particularly when the concrete is subjected to wide temperature ranges and heavy vehicular traffic. Thus there has been a need for practical and effective asphalt concrete testing system in which compacted bituminous specimens could be water conditioned while selectively temperature conditioned and load conditioned. The present invention aims to fill this need so that the best performing asphalt concrete mixture for a given location can be more accurately selected.

SUMMARY OF THE INVENTION

The present invention tests a cylindrical specimen on a test stand in an environmental cabinet having a relatively wide range of controlled hot and cold temperatures. The specimen is isolated from direct contact with the cabinet atmosphere by an impervious shroud and by end platens which are connected to an external fluid circulating system which provides a differential pressure across the specimen to cause controlled fluid (air or water) flow through the specimen. The specimen is axially loaded via a load cell by a pulsating pneumatic actuator on the test stand. A pair of transducers is mounted on the specimen to measure resulting axial deformation of the specimen. Data is transferred from the load cell and transducer to a microcomputer station for analysis and the desired calculations by suitable software.

DETAILED DESCRIPTION OF THE INVENTION

Figure 1:
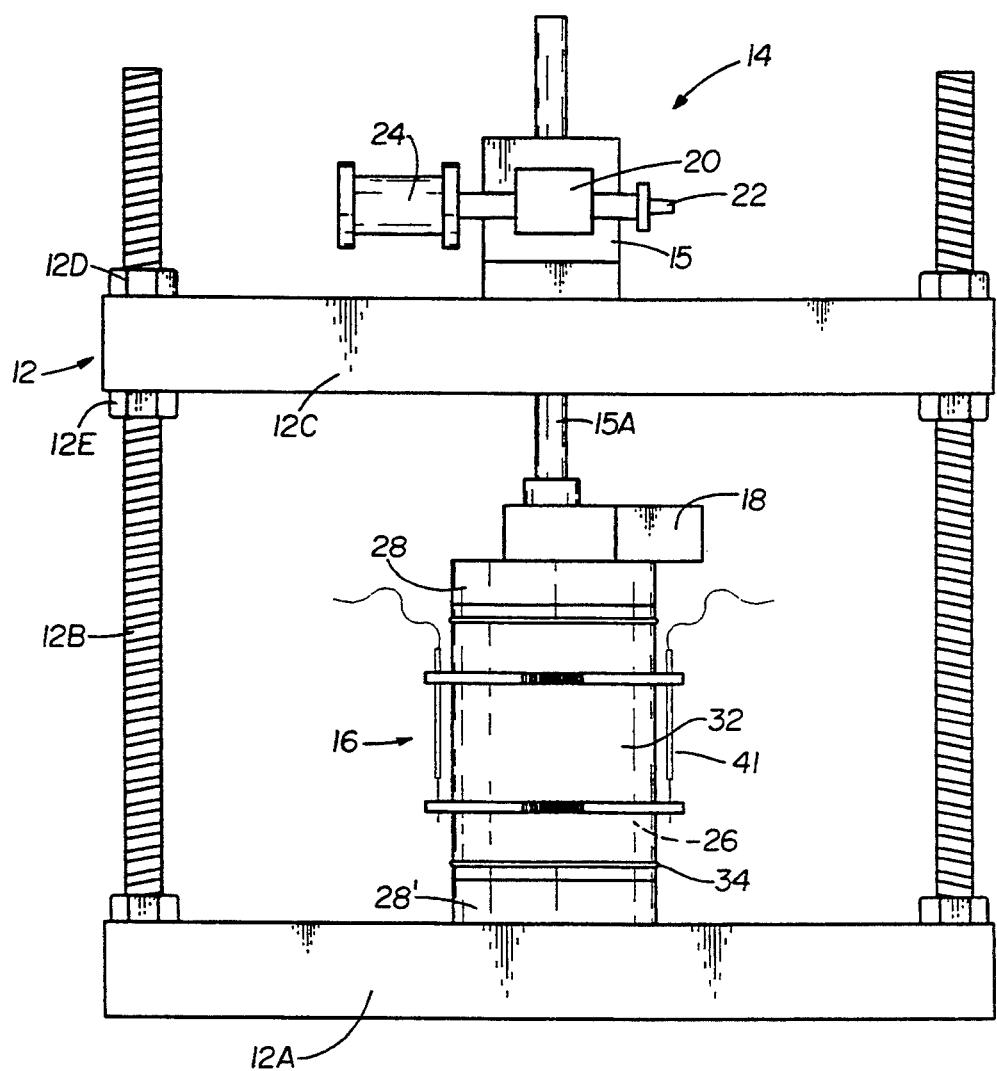
FIG. 1 is a front elevational view showing the test station apparatus in accordance with the invention.
Figure 2:
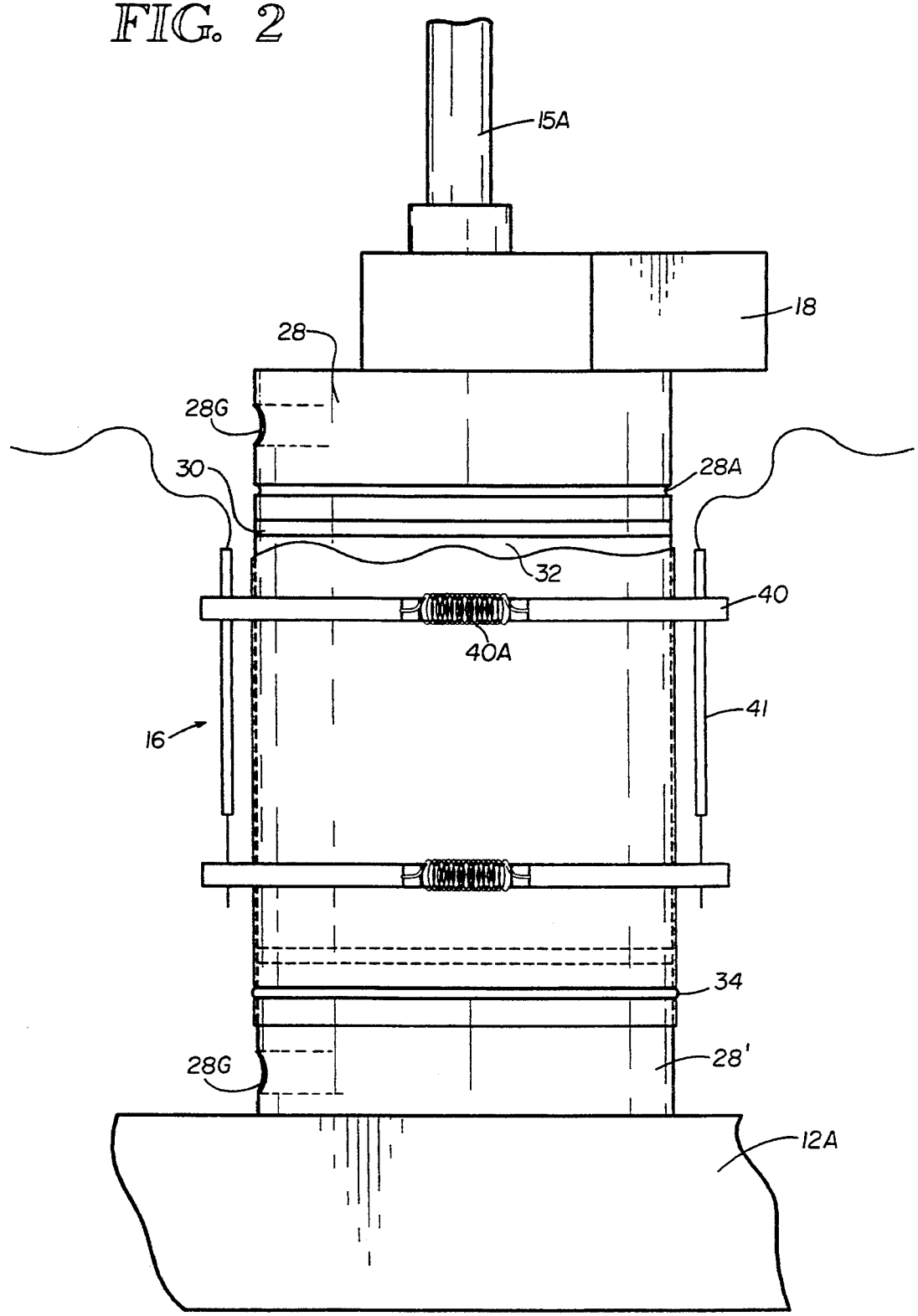
FIG. 2 is a front elevational view showing the specimen holder to an enlarged scale and with part of the membrane sleeve broken away.
Figure 3:
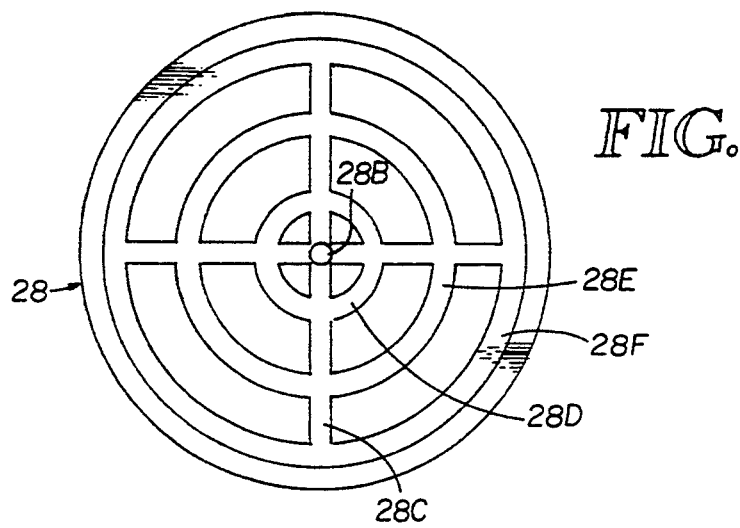
FIG. 3 is a bottom plan view of the upper platen.
Figure 4:
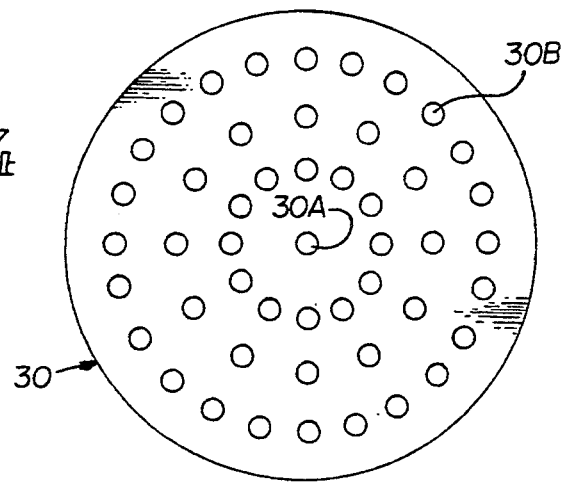
FIG. 4 is a plan view of one of the spacers.
Figure 5:
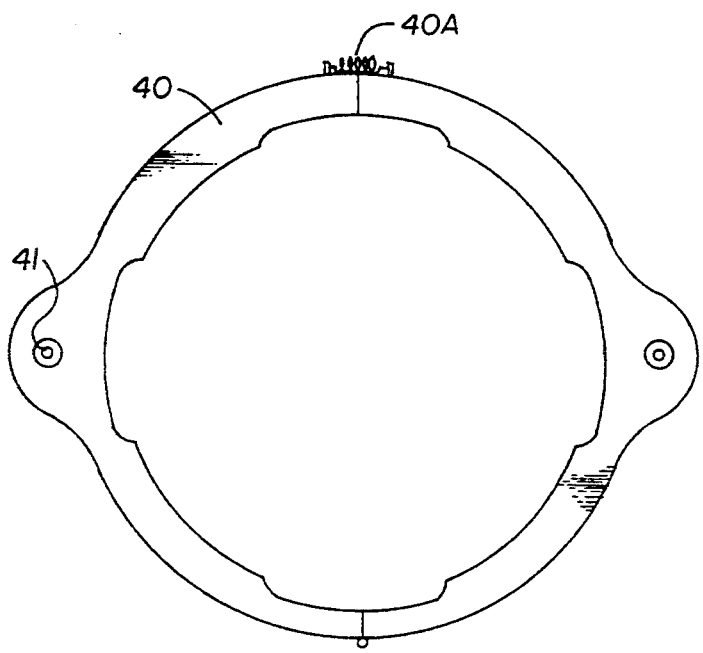
FIG. 5 is a top plan view of the upper clamping yoke.
Figure 6:
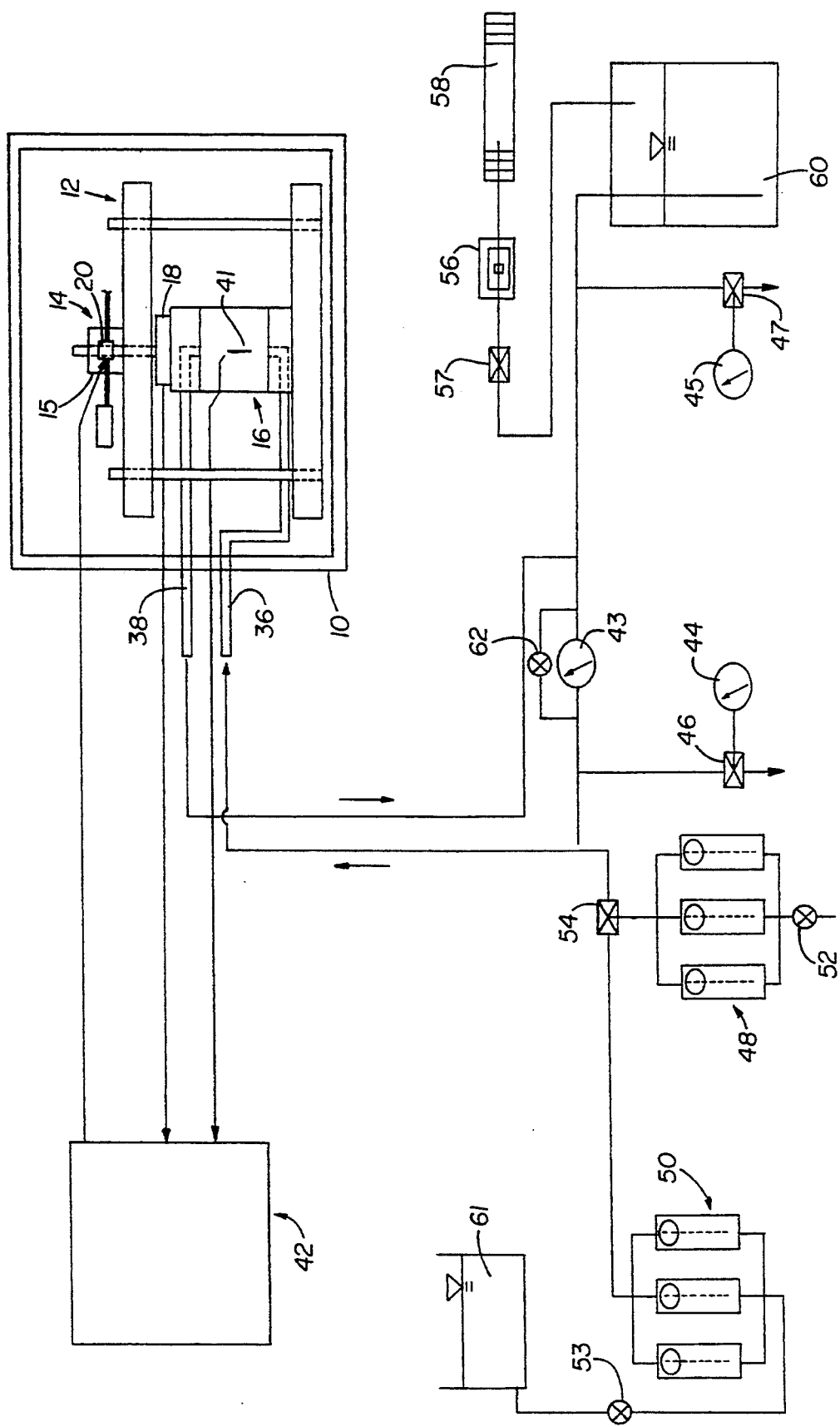
FIG. 6 is a schematic of the testing system of the invention.

The system testing utilizes a suitable environmental conditioning cabinet 10 such as a Cincinnati Sub-Zero Z-8-5 cabinet having a heating and refrigeration system with a programmable temperature controller preferably achieving temperatures in the range of a $-30°$ C. to $175°$ C., for example. The air for the cabinet chamber is circulated by a fan located in a conditioning plenum at the rear of the chamber. The conditioned air is discharged from the plenum near the top of the chamber, circulated throughout the chamber, and returned to the bottom of the plenum. Preferably the conditioning chamber has a setpoint accuracy of $\pm 0.5°$ C.

Mounted in the conditioning cabinet is a specimen handling station comprising a load frame 12, load applying apparatus 14, and a specimen holder 16. The load frame 12 has a rectangular base plate 12a on which are mounted four threaded tie rods 12b which extend upwardly through a top plate 12c. Adjustment of the height of the top plate is accomplished by way of pairs of nuts 12d, 12e threaded on the tie bolts to engage the top and bottom faces of the top plate.

The load applying apparatus 14 comprises a double-acting air cylinder unit 15 bolted onto the top plate 12c and having its piston rod 15a projecting downwardly through the top plate to a load cell 18 preferably having a range up to 1,000 lbs (454 kg). The air cylinder 15 may have a piston diameter of 4 inches and at least a 3 inch stroke, and is controlled by a solenoid operated servo-valve 20. This servo-valve is mounted on the air cylinder unit 15 and has an input fitting 22 for a compressed air supply line and an exhaust port connected to a muffler 24, and connects with the ends of the air cylinder 15. The preferred operating range of the servo-valve is 80 to 150 psi.

The specimen holder 16 forms an isolation sandwich with a cylindrical specimen 26 and comprises a pair of top and bottom aluminum platens 28, 28' a pair of thin Teflon spacers 30 between the specimen and the platens, a rubber membrane sleeve 32 enveloping the specimen, and a pair of elastic 0-rings 34 clamping end portions of the sleeve 32 to the platens 28 at peripheral grooves 28a in the platens. The specimen 26 is preferably 4 inches in diameter and 4 inches high, and it is recommended that the specimen be cored from a slab of compacted bituminous concrete prepared with the use of a rolling wheel compactor or as molded if prepared by kneading or gyratory compaction.

Each of the platens 28, 28' has a center passage 28b communicating at its inner end by radial grooves 28c with three concentric annular grooves 28d-f facing inwardly toward a respective end of the specimen. The center passages 28b communicate at their outer end with threaded radial ports 28g to which supply and discharge lines 36, 38 are connected. The Teflon spacers 30 each have a center hole 30a and three concentric groups of holes 30b arranged to register with the annular grooves 16*d-f* in the platens 28. The spacers 30 are included primarily because of the near frictionless characteristic of Teflon at the contact surfaces with the platens 28, 28' and end faces of the specimen. Also, the top spacer 30 collects any stripped asphalt from the specimen which would otherwise stick to the bottom of the top platen during the water conditioning process and change its serviceability condition.

Before the specimen is mounted on the test stand a coating of silicone cement is applied as a sealer between the outer cylindrical face of the specimen and the membrane 32 as by squirting a bead of the silicone inside the membrane 32 and smoothing the membrane over the specimen. After the silicone has set, the specimen and membrane are positioned with end portions of the membrane overlapping the periphery of the spacers 30 and enough of the periphery of the platens to permit the 0-rings 34 to fit over the end portions of the membrane 32 and clamp them into the grooves 28a in the platens.

The platens 28, 28' are preferably 4 inches in diameter and 1.5 inches thick with the grooves 28*c-f* being 3/16 inches wide and 3/32 inches deep. The Teflon spacers 30 are preferably also 4 inches in diameter and can have a thickness of about 0.13 inches.

A pair of hinged yokes 40 are applied as clamps over the membrane 32 on the specimen in spaced relation along the length of the specimen. Each yoke is held in closed clamping position by a spring 40a and firmly grips the specimen via the silicone cement and membrane in portions of the four quadrants. A pair of linear variable differential transducers (LVDT) units 41 are mounted at diametrically opposite positions between the clamps 40a. Leads (not shown) from the LVDTs, the load cell 18, and the solenoid for the servo-valve 20 are connected to terminals of a micro-computer system 42 external of the cabinet 10.

The supply and discharge lines 36, 38 to the bottom platen 28' and from the top platen 28, respectively, pass through the cabinet 10 to an external control panel in a fluid conditioning system presenting a differential pressure gauge 43, inflow and outflow pressure gauges 44–45, on-off control handles for respective control valves 46–47 for the gauges 44–45, an air flow meter unit 48, a water flow meter unit 50, on-off control handles for respective control valves 52, 53 for the air and water flowmeters, a selector control lever for a selector valve 54, a control knob for a vacuum regulator 56, and an on-off control handle for a vacuum control valve 57.

Referring to the schematic for the fluid conditioning system, it is seen that the flow circuit includes a supply branch connected to the supply line 36 to the bottom platen 28', and a vacuum branch connected to the discharge line 38 from the top platen 28. This vacuum branch has a vacuum pump 58, the vacuum regulator 56, the on-off vacuum control valve 57, and a water trap 60 in series, and also includes the gauge 45 and valve 47 in an off-shoot. The supply branch includes the selector valve 54, the air flow meter unit 48 and respective control valve 52, the water flow meter unit 50 and respective control valve 53, and a distilled water source 61. The vacuum and supply branches have off-shoots connected to the differential pressure gauge 43 and may be cross-connected via a valve 62. The differential pressure between the vacuum (discharge) branch and the supply branch causes the desired flow through the specimen.

The air flow meter unit 48 and water flow meter unit 50 each preferably contain three meters of different sizes. For example, the air flow meters may have flow ranges of 100 to 1000 $cm^3$/min., 1 to 10 scfh, and 15 to 150 scfh, and the water flow meters may have flow ranges of 2 to 30 $cm^3$/min., 0.5 to 12 gph, and 6 to 60 gph. The vacuum pump 58 preferably should be able to provide a continuous vacuum source of at least 25 in. Hg at 1 scfm. The water source 60 should be a source able to supply distilled water at a rate of at least a gallon per hour.

Suitable software is provided to operate as a closed-loop, servo-valve controller and data acquisition/reduction interface to be used with a suitable computer. The software is capable of inducing a specified load on the specimen by the pneumatic cylinder unit 15 by controlling the servo valve 20 in a closed loop control system including the load cell 18, which can be manually or automatically controlled. A proportional-integral-derivative feedback algorithm used to control a compressive load pulse induced by the cylinder unit 15 on the specimen. Preferably the load pulse has a form close to a haversine wave form and preferably has a duration of 0.1 second followed by a 0.9 second dwell time. Deformation data from the LVDTs is continuously collected and correlated with the load data.

The load and deformation data are preferably displayed graphically. Graphical display of the deformation data may consist of a trace representing the response of the LVDTs 41. The load data is preferably displayed in digital form including the magnitude of current and pulse (differential) load shown in pounds. The deformation display preferably includes the average elastic(resilient) deformation measured by the LVDTs and is shown in engineering units of inches and strain. The software is preferably capable of calculating and displaying the results of a ECS modulus test by providing a tabular summary of the results including the test time, gage length, pulse (differential) load, pulse stress, elastic deformation, elastic strain, ECS modulus, and the standard deviation and coefficient of variation for the modulus results. A typical test procedure will now be described.

To determine the air permeability of a specimen after it has been mounted in testing position within the cabinet enveloped in the sleeve 32, the selector valve 54 is moved to connect with the air flowmeter unit 48 and the air valve 52 is opened. A desired pressure differential is then applied across the specimen by opening vacuum control valve 57 and adjusting the vacuum regulator 56 after starting the vacuum pump 58. The vacuum adjustment is set to obtain the lowest pressure differential possible across the specimen with the temperature in the environmental chamber set at 25° C. The air flow through the specimen is read at the air flow meter 48 and the pressure differential is read at gauge 43. The test is repeated several times at different differential pressures and the air permeability is then calculated. At this point the initial ECS modulus is determined.

Then the specimen undergoes a wetting procedure in which distilled water is pulled by the vacuum at the upper side of the specimen through the specimen after adjusting the selector valve 54 so that the distilled water source is in communication with the lower end of the specimen. The vacuum regulator is adjusted such that there is a vacuum of about 20 in. Hg, and the wetting procedure is preferably continued for a period of 30 minutes at 25° C. The water permeability of the specimen is then calculated.

After completion of the specimen wetting process and initial water permeability testing, a hot climate conditioning procedure is commenced with the temperature of the environmental chamber initially set and maintained at 60° C. for a period of 5 hours. During this period the vacuum is set at 10 in. Hg and the water flow through the specimen is set to be between 2 and 5 cc/min. At the end of the 5 hour period, the temperature setting is reduced to 25° C. for an additional 2 hours. Throughout the total 7 hour period, a repeated axial compressive load of 200 lbs. is applied to the specimen by the pneumatic cylinder, preferably in a one second haversine wave cycle in which the pressure is on for 0.1 second and is off for 0.9 second. At the end of the 7 hour cycle, the ECS modulus and water permeability is measured. The described procedure is repeated for two more 7 hour cycles, and the ECS modulus and water permeability are again measured at the end of the second and third such cycles. If the specimen is also to be tested for cold climates, the temperature of the environmental chamber is changed to −18° C. at the completion of the third hot climate conditioning cycle of 7 hours. This lowered temperature is maintained for 5 hours and is then raised to 25° C. for another 2 hours. As before, water is continuously pulled through the specimen under a vacuum of 10 inches of Hg. At the end of this 7 hour cold climate conditioning cycle the ECS modulus and water permeability are again calculated. The specimen is then removed. It will be appreciated that the time periods referred to above are by way of example and may be varied.

After removal the stripping rate of the specimen is preferably determined. This is done by placing the specimen between two bearing plates of a loading jack on a mechanical or hydraulic testing machine and applying a compressive load to the specimen at a constant rate of movement until a vertical crack appears. The specimen is then removed from the loading jack and pulled apart at the crack for inspection of the interior surface of the specimen for stripping as compared to the standard pattern.

From the foregoing it will be appreciated that, although specific embodiments of the invention have been described herein for purposes of illustration, various modifications may be made without deviating from the spirit and scope of the invention. Accordingly, the invention is not limited except as by the appended claims.

We claims:

1. A testing system for cylindrical compacted asphalt concrete specimens having a longitudinal center axis perpendicular to opposite end faces, said system comprising;
    a test chamber;
    temperature control means for selectively varying the temperature of the atmosphere in said chamber;
    isolating means for shrouding and holding a specimen in testing position in said chamber with its pores isolated from communication with the chamber atmosphere, said isolating means including supply and discharge ports communicating with respective end faces of the specimen being tested;
    a load cell seating on said isolating means;
    compression loading means arranged in said chamber to engage said load cell such as to selectively axially compress a specimen in said testing position in a load/no-load cycle;
    and fluid circulating means connected to said ports for selectively passing air or water endwise through the specimen being tested.

2. A testing system according to claim 1 in which a test stand is located in said chamber for supporting a specimen in testing position shrouded by said isolating means, and in which said compression loading means is mounted on said test stand for engaging said isolating means to axially compress the specimen in said load/no-load cycle.

3. A testing system according to claim 2 in which said compression loading means comprises a double-acting pneumatic cylinder unit mounted on said stand and supplied with pressurized air via an electrically controlled servo-valve for alternately charging and discharging the ends of the cylinder unit.

4. A testing system according to claim 1 in which deformation transducer means is applied to said specimen for indicating the axial deformation of the specimen responsive to said compression loading means.

5. A testing system according to claim 1 in which deformation transducer means is mounted on said specimen via the portion of said isolating means which shrouds the rounded portion of the specimen.

6. A testing system for cylinder compacted asphalt concrete specimens having a longitudinal center axis perpendicular to opposite end faces, said system comprising;
    a test chamber;
    temperature control means for selectively varying the temperature of the atmosphere in said chamber;
    isolating means for shrouding and holding a specimen in testing position in said chamber with its pores isolated from communication with the chamber atmosphere, said isolating means including supply and discharge ports communicating with respective end faces of the specimen being tested;
    compression loading means arranged in said chamber to engage said load cell isolating means such as to selectively axially compress a specimen in said testing position in a load/no-load cycle;
    and fluid circulating means connected to said ports for selectively passing air or water endwise through the specimen being tested, said fluid circulating means including a supply circuit connected to said supply port and a discharge circuit connected to said discharge port, said supply circuit including a water source, an air source, and a selector valve exterior of said chamber for selecting either of said sources, and said discharge circuit including a vacuum source exterior of said chamber whereby a differential pressure is created between the ends of the specimen being tested, and a vacuum regulator.

7. A testing system according to claim 6 in which said supply circuit includes flow meters exterior of said chamber for reading the flow rate of air and water circulated through the specimen.

8. A testing system according to claim 7 in which said supply circuit and discharge circuit each include a respective pressure gauge exterior of said chamber.

9. A testing system according to claim 6 in which said supply and discharge circuits are connected to a differential pressure gauge exterior of said chamber.

10. A testing system for cylindrical compacted asphalt concrete specimens having a longitudinal center axis perpendicular to opposite end faces, said system comprising;

a test chamber;

temperature control means for selectively varying the temperature of the atmosphere in said chamber;

isolating means for shrouding and holding a specimen in testing position in said chamber with its pores isolated from communication with the chamber atmosphere, said isolating means including supply and discharge ports communicating with respective end faces of the specimen being tested, and including top and bottom cylindrical platens with respective annular grooves, an elastic envelope covering the outer rounded surface of said specimen and having end portions overlapping said annular grooves, and clamping rings surrounding said end portions and seated in said annular grooves, said platens having through passages communicating with said ports and end faces;

compression loading means arranged in said chamber to engage said isolating means such as to selectively axially compress a specimen in said testing position in a load/no-load cycle;

and fluid circulating means connected to said ports for selectively passing air or water endwise through the specimen being tested.

11. A testing system according to claim 10 in which thin discs of polytetrafluoroethylene are positioned between said platens and the ends of the specimen, said discs having through passages exposed to the ends of the specimen and to the passages in said platens.

12. A testing system according to claim 10 in which a load cell seats on the upper one of said platens, and in which said compression loading means acts on said load cell.

13. A testing system according to claim 10 in which deformation transducer means is clamped to said envelope and the underlying specimen at two spaced levels along the length of the specimen.

14. A testing system for cylindrical compacted asphalt concrete specimens having a longitudinal center axis perpendicular to opposite end faces, said system comprising;

a test chamber;

temperature control means for selectively varying the temperature of the atmosphere in said chamber;

isolating means for shrouding and holding a specimen in testing position in said chamber with its pores isolated from communication with the chamber atmosphere, said isolating means including supply and discharge ports communicating with respective end faces of the specimen being tested, and said isolating means including an elastic sleeve bonded to said specimen along a part of its length;

compression loading means arranged in said chamber to engage said isolating means such as to selectively axially compress a specimen in said testing position in a load/no-load cycle;

and fluid circulating means connected to said ports for selectively passing air or water endwise through the specimen being tested.

15. A testing system according to claim 14 in which deformation transducer means is clamped over said sleeve in said bonded part.

* * * * *